US011826502B2

(12) United States Patent
Joechle et al.

(10) Patent No.: US 11,826,502 B2
(45) Date of Patent: Nov. 28, 2023

(54) OXYGENATOR WITH A HOUSING WALL

(71) Applicant: Xenios AG, Heilbronn (DE)

(72) Inventors: Knut Joechle, Neckarsulm (DE); Sebastian Koehler, Nordheim (DE)

(73) Assignee: Xenios AG, Heilbronn (DE)

(*) Notice: Subject to any disclaimer, the term of this patent is extended or adjusted under 35 U.S.C. 154(b) by 1060 days.

(21) Appl. No.: 16/324,202

(22) PCT Filed: Jun. 14, 2017

(86) PCT No.: PCT/DE2017/000162
§ 371 (c)(1),
(2) Date: Feb. 8, 2019

(87) PCT Pub. No.: WO2018/028727
PCT Pub. Date: Feb. 15, 2018

(65) Prior Publication Data
US 2019/0209763 A1 Jul. 11, 2019

(30) Foreign Application Priority Data

Aug. 9, 2016 (DE) ................ 10 2016 009 599.7
Oct. 5, 2016 (DE) ................ 10 2016 011 946.2

(51) Int. Cl.
*A61M 1/16* (2006.01)
*A61M 1/36* (2006.01)
(Continued)

(52) U.S. Cl.
CPC .......... *A61M 1/1698* (2013.01); *A61F 7/007* (2013.01); *A61M 1/32* (2013.01); *A61M 1/3666* (2013.01);
(Continued)

(58) Field of Classification Search
CPC ............. A61F 7/007; A61F 2007/006; A61F 2007/0088; A61M 1/1698; A61M 1/32;
(Continued)

(56) References Cited

U.S. PATENT DOCUMENTS 3,112,746 A * 12/1963 Gewecke ............. A61M 1/32
422/47
3,211,148 A 10/1965 Galajda, Jr.
(Continued)

FOREIGN PATENT DOCUMENTS

CN 104136597 A 11/2014
DE 1 096 554 B 1/1961
(Continued)

OTHER PUBLICATIONS

Independent_Definition_Meaning_-_Merriam-Webster.pdf (Year: 2022).*

(Continued)

*Primary Examiner* — Benjamin J Klein
(74) *Attorney, Agent, or Firm* — Collard & Roe, P.C.

(57) ABSTRACT

An oxygenator with a housing wall, which delimits a housing space with a blood inlet and a blood outlet, a gas inlet and a gas outlet, has a heating element which is arranged in the oxygenator between blood inlet and blood outlet in order to control the temperature of blood flowing through the housing space. For this purpose, the oxygenator has a radiation source and a receiver. The radiation source can be an infrared emitter and the receiver a matte-black surface, or the radiation source is an induction coil and the receiver has a material capable of induction. In a method for regulating the heat output on a heating element of an oxygenator, the through-flow of the blood through the oxygenator and the power of a pump acting on the through-flow are measured, and the heating power is adjusted in accordance therewith.

18 Claims, 4 Drawing Sheets

(51) Int. Cl.
*A61M 1/32* (2006.01)
*A61F 7/00* (2006.01)

(52) U.S. Cl.
CPC . *A61F 2007/006* (2013.01); *A61F 2007/0088* (2013.01); *A61M 2205/36* (2013.01); *A61M 2205/368* (2013.01); *A61M 2205/50* (2013.01)

(58) Field of Classification Search
CPC ............ A61M 1/3666; A61M 2205/36; A61M 2205/368; A61M 2205/50
See application file for complete search history.

(56) References Cited

U.S. PATENT DOCUMENTS

| | | | |
|---|---|---|---|
| 3,929,414 A | 12/1975 | Leonard | |
| 5,817,279 A * | 10/1998 | Eilers | A61M 1/1698 422/46 |
| 6,261,261 B1 * | 7/2001 | Gordon | A61M 5/44 604/113 |
| 7,153,285 B2 | 12/2006 | Lauman et al. | |
| 9,644,234 B2 | 5/2017 | Pipper et al. | |
| 2003/0135250 A1 * | 7/2003 | Lauman | A61M 1/1696 607/104 |
| 2008/0058709 A1 * | 3/2008 | Da Silva Freitas | A61M 5/142 604/23 |
| 2012/0277654 A1 | 11/2012 | Olson et al. | |
| 2013/0081621 A1 * | 4/2013 | Korneff | A61M 16/1095 128/203.27 |
| 2013/0280692 A1 * | 10/2013 | Gourlay | A61M 1/262 422/46 |
| 2017/0128258 A1 * | 5/2017 | Diller | A61F 7/007 |
| 2017/0252501 A1 * | 9/2017 | Pouchoulin | A61M 1/369 |

FOREIGN PATENT DOCUMENTS

| | | |
|---|---|---|
| DE | 10 2011 052188 A1 | 1/2013 |
| EP | 0 621 047 A2 | 10/1994 |
| EP | 0 765 683 B1 | 7/1998 |
| EP | 2 143 453 A2 | 1/2010 |
| EP | 2 848 269 A1 | 3/2015 |
| WO | 2004/105589 A2 | 12/2004 |
| WO | 2012/013925 A2 | 2/2012 |
| WO | 2013/012776 A1 | 1/2013 |

OTHER PUBLICATIONS

Individually_Definition_Meaning_-_Merriam-Webster.pdf (Year: 2022).*
International Search Report in PCT/DE2017/000162 dated Oct. 17, 2017.

* cited by examiner

OXYGENATOR WITH A HOUSING WALL

CROSS REFERENCE TO RELATED APPLICATIONS

This application is the National Stage of PCT/DE2017/000162 filed on Jun. 14, 2017, which claims priority under 35 U.S.C. § 119 of German Application Nos. 10 2016 009 599.7 filed on Aug. 9, 2016 and 10 2016 011 946.2 filed on Oct. 5, 2016, the disclosures of which are incorporated by reference. The international application under PCT article 21(2) was not published in English.

BACKGROUND OF THE INVENTION

1. Field of the Invention

The invention concerns an oxygenator with a housing wall that delimits a housing space with a blood inlet, a blood outlet, a gas inlet and a gas outlet, and a heating element to control the temperature of the blood flowing through the housing space.

2. Description of the Related Art

Oxygenators are medical gas exchangers that are mainly used in cardiopulmonary therapies lasting several days or during operations. Another application, for example, is dialysis. In addition to gas exchange, these oxygenators often also offer the possibility of controlling the temperature of the blood flowing through a housing space of the oxygenator. As a rule, the blood in the oxygenator is heated because the blood temperature in the extracorporeal circulation, that is to say, outside the patient's body, decreases over time and the patient becomes hypothermic. In addition to this heating, it is also possible to cool the blood temperature during heart surgery in order to lower the body temperature.

Heater-coolers (HC-devices) are used to regulate a patient's blood and body temperature during an operation, or during longer therapy sessions with gas exchangers. A heater-cooler (HC-device) is an external device that is connected to an oxygenator by way of hoses. In the HC-device, water is passed through metal struts and heated or cooled. The water is then led to the oxygenator and flows through heat exchanger mats made of hollow fibers, or, in particular, primarily metallic channels in the oxygenator, past which the blood is led. Such an oxygenator is described in EP 765 683 B1.

Such oxygenators are practical in use. However, the heater-cooler devices that are used operate with a water bath that can become contaminated when in use, and can contaminate the air in the environment. The HC-devices are very heavy and immobile on account of the water bath and the cooling equipment. They must be cleaned regularly since they are used in the vicinity of the oxygenator, and therefore in hospitals, e.g. in operating theatres or intensive care units.

SUMMARY OF THE INVENTION

The invention is therefore based on the object of developing an oxygenator further. This object is achieved with a generic oxygenator, in which the heating element has a radiation source and a receiver, which converts the radiation of the radiation source into heat.

The invention is based on the knowledge that heating in the oxygenator between blood inlet and blood outlet by means of fluid-carrying tubes requires a complex additional device. Since the heating element has a radiation source and a receiver, an HC-device can be dispensed with, and only one voltage source is required for the radiation source.

Between the blood inlet and the blood outlet, liquids other than blood, such as blood substitute solutions, such as priming liquids, or medical solutions such as buffer solutions with added medication, can also be heated in the oxygenator. When the term blood temperature is used in what follows, it also refers to such liquids.

The radiation source makes it possible to keep the blood temperature within a range of body temperature, and thus between 36 and 38° C. Care must be taken that the temperature does not exceed 40° C. at any point of the device. Since the blood cools the receiver, heating of the receiver takes place at 35° C. to 60° C., depending on the blood flow.

A first variant stipulates that the radiation source emits infrared light and that the receiver has a dark, preferably a matte-black, surface. The dark surface can be formed by the blood itself, so that the infrared light radiation emits heat energy to the blood when it impinges onto the blood. Thus the dark surface of the blood forms the receiver. Additionally or alternatively, the receiver can have dark surfaces arranged between the radiation source and the blood, to heat itself and then the blood. However, the receiver surfaces can also be arranged such that the infrared light impinges onto the receiver surface through the blood, thereby heating the blood directly on the one hand, and indirectly by way of the heated receiver surface on the other.

The spectral range between $10^{-3}$ m and $7.8*10^{-7}$ m (1 mm and 780 nm) is designated as infrared. This corresponds to a frequency range from $3*10^{11}$ Hz to approx. $4*10^{14}$ Hz (300 GHz to 4000 THz). Near-infrared NIR (IR-A with wavelengths between 0.78 and 1.4 µm, and IR-B with wavelengths between 1.4 and 3.0 µm), and also medium-infrared NIR (IR-C with wavelengths between 3 and 50 µm) are particularly suitable.

Here the penetration depth of the infrared light is dependent on the wavelength of the radiation and the material properties of the surfaces that are impinged, as well as, if necessary, the filtering by housing parts and a blood flow located between the radiation source and the receiver.

Since oxygenators are generally made of a transparent material such as polyurethane, oxygenators of known art can be used in which a source of infrared radiation is arranged outside the housing, which radiates through the outer wall of the housing.

Receivers of this type can be integrated into any type of medical gas exchanger so as to heat the blood. For this purpose, surfaces made of dark, particularly heat radiation absorbing, material are produced on the oxygenator or in the oxygenator, or films are used, which are arranged in the oxygenator housing. In addition to symmetrical arrangements of the receivers in the housing, flow-adapted arrangements can also be used, which make it possible to provide particularly large receiver surfaces in regions with a large volumetric flow.

It is advantageous if the oxygenator still has a transparent region, through which a medic can visually check the condition of the blood inside the oxygenator.

In order to vary the intensity of the infrared radiator, it is proposed that the infrared radiator has a plurality of radiation sources, such as a plurality of dimmable lamps, ions, or lasers, or filters, which can preferably be controlled individually so as to adjust the intensity of the heating. It is therefore advantageous if, on the one hand, the wavelength of the radiation source can be adjusted. Here the wavelength can be varied with an algorithm such that different penetration depths are achieved.

On the other hand, it is advantageous if the absorption capacity of the receiver can be altered in a regulated manner. This can be achieved, for example, by changing the colour color of the receiver, or by changing the position of the receiver relative to the radiation source. For this purpose, for example, a flap mechanism or a directional screen can be provided, in order either to direct the infrared light to different points of the gas exchanger, or to absorb more or less infrared light with the receiver. In particular, the irradiation with the radiation source can be aligned in such a way that it irradiates different regions of the oxygenator in a time-dependent manner. This results in an itinerant form of irradiation. In the case of automatic regulation, these data are reported to the control console and used to control or regulate the heating power.

An alternative embodiment stipulates that the radiation source has an induction coil and the receiver is made of a material that is capable of induction. Copper or an iron alloy are examples of materials that are capable of induction. By this means inductive heating is possible.

For example, the radiation source can be a large flat single-layer coil of high-frequency litz wires that generate a high-frequency alternating magnetic field. Together with capacitors, this coil forms a floating circuit, which is set into resonance by one or a plurality of switching transistors. The power management can be implemented by means of a variety of circuit concepts, such as a transistor circuit, excitation frequency control, and pulse-width control. A particular advantage of inductive heating is that the power is adjusted very precisely.

In a similar manner to a radiation source with infrared light, a directional screen or a hemispherical protective screen around the radiation source can also be stipulated for a radiation source in the form of an induction coil. This enables magnetic scattering or interference radiation to be prevented. By this means, the alternating magnetic field or electric field remains spatially delimited.

To avoid overheating, the radiation source can have a fan. These measures enable the oxygenator and receiver to be regulated very precisely to the desired temperature.

The receiver can be arranged in the outer wall of the oxygenator so as to heat the blood flowing in the housing space. However, it is particularly advantageous if the receiver is arranged in the housing space. This allows the use of large receiver surfaces and thus a small temperature difference between receiver surface and blood. This prevents damage to the blood.

However, depending on the application, the receiver can also be arranged in the housing wall. This enables a simple form of construction and, especially in the case of flat hollow fiber mats laid in parallel, good heat transfer from the receiver to the blood.

Semi-permeable materials such as, in particular, membranes, are usually arranged between the gas regions and the blood regions of the oxygenator. These membranes can be flat films or hollow fibers.

To hold flat or tubular membranes in an oxygenator, potting materials, such as plastic, are used. It is therefore advantageous if the oxygenator has a potting layer for holding fluid lines, and the receiver is arranged in this potting layer, or at least also in this potting layer.

When heating the blood, care must be taken to ensure that no damage to the blood occurs, even if the blood only overheats in certain regions. It is therefore proposed that the oxygenator should have at least one temperature sensor. It is particularly advantageous if temperature sensors are provided at various points in the oxygenator so as to ensure that temperatures are not too high in any region. The temperature sensors should therefore also be located, if possible, at least in regions in which the blood flow velocity is slower than in other regions of the housing space, or in which the blood flow velocity is slower than the average blood flow velocity in the housing space, and in which there can therefore be a risk of overheating.

The temperature of the receiver can be varied by way of the voltage applied to the radiation source, and it is therefore useful if the oxygenator has a temperature regulation device.

It is advantageous if the temperature is measured at one or a plurality of points at defined time intervals. The frequency can be specified by means of an algorithm. By this means the risk of overheating can be avoided. This is called pulse width modulation.

In many cases, the oxygenator is connected to a control console that can be used to control the flow of gas or blood through the oxygenator, for example. Such a control console includes control electronics for purposes of controlling or regulating the use of the oxygenator. The radiation source and/or the receiver can also be controlled by way of such a control console, and this activation can be regulated as a function of other data or process parameters available on the control console, such as blood or gas flow, and the temperature in the oxygenator.

A particularly advantageous variant of embodiment stipulates that the temperature regulation individually adjusts or regulates the temperature of the receiver at various locations. This makes it possible to provide heating of differing intensity at various locations on the basis of the typical flow velocities in the oxygenator.

For this purpose, it is stipulated that the receiver delivers a different heating power at various locations in the housing space. The heating power can be varied according to blood flow, blood velocity, gas flow and gas velocity.

One variant of embodiment stipulates that the receiver has a plurality of receiver components that can be positioned at various locations in the oxygenator. These receiver components can then be individually controlled, independently of one another, so as to achieve a certain heating intensity distribution in the oxygenator and, if necessary, to alter it during operation of the oxygenator.

However, a receiver can also be stipulated that has a plurality of receiver components that can be controlled independently of one another.

An additional effect is achieved by arranging the receiver in the oxygenator between the gas inlet and the gas outlet so as to control also the temperature of the gas flowing through the housing space. In particular, this can prevent condensation.

A simple embodiment of an oxygenator stipulates an oxygenator with a housing wall that has only four fluid passages leading to the external environment. Of these, two fluid passages can be used for the gas inlet and outlet and two fluid passages can be used for the blood inlet and outlet.

A connector identifies the possibility of connection of hoses to the oxygenator. A part of the heating element can be arranged in such a connector.

It is advantageous if the oxygenator has a heat conduction device for heat conduction to the heating element. For example, if the heating element is designed as a heatable metal part, it can be surrounded by a heat conduction device, so as to increase the surface area, or to prevent contact between the blood and the metal part. This heat conduction device then conducts the heat from the heating element to a surface area that is in contact with the blood, and is preferably larger than the surface area of the heating element. Such a surface area can be the surface area of a grid or film.

The heat conduction device should in particular serve to enable the distribution of heat from the heating element in the housing space.

An advantageous variant of embodiment stipulates that the oxygenator has an insulating layer or a vacuum layer, so as to insulate the blood flowing in the housing space. An insulating layer and a reflective layer can also be designed such that they can be opened so as to release heat easily once again, so as to cool the oxygenator and thereby avoid overheating. In addition, the layers can also be arranged partially, or can have the ability to be arranged partially.

In order to reflect heat radiation from the blood flowing in the housing space back to the blood, and thus to minimize also the emission of heat radiation from the oxygenator, it is proposed that the oxygenator has a reflective layer. Such a reflective layer can be, for example, a metal film or a polished surface.

In order to be able to observe the blood flow in the oxygenator, it is advantageous if the insulating and/or reflective layer is transparent or at least partially transparent. For this purpose, for example, a closely meshed grid, a perforated film, or a film with transparent window regions can be provided.

A simple variant of embodiment, which is particularly suitable for cylindrical oxygenators, stipulates that the oxygenator has a central opening with a dome-shaped retaining element. The dome-shaped retaining element can then also have the heating element and in particular the radiation source, so as to heat the blood flowing in the housing space.

In terms of method, the object underlying the invention is achieved by a method for regulating the heat output from a heating element of an oxygenator, in which the flow of blood through the oxygenator and the power of a pump governing the through-flow are measured, and the heating power is adjusted in accordance therewith. The receiver can have a plurality of receiver components that can be controlled separately from one another, and which are controlled such that the temperature difference between the temperature of the blood at the receiver component, and the temperature of the receiver component, does not exceed a predefined value. These methods are particularly suitable for an oxygenator in accordance with one of the preceding claims.

BRIEF DESCRIPTION OF THE DRAWINGS

Examples of embodiment of inventive oxygenators are shown in the figures and are described in more detail below. Here.

DETAILED DESCRIPTION OF THE PREFERRED EMBODIMENTS

Figure 1:
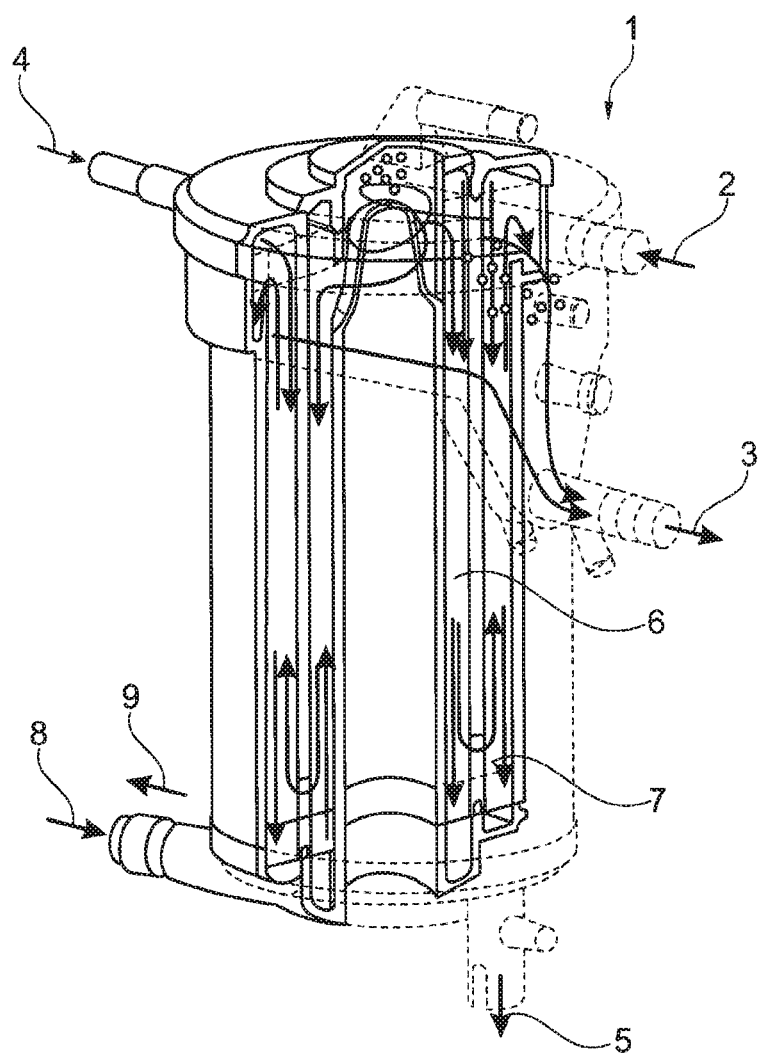
FIG. 1 shows an oxygenator of known art with blood, gas and water flows.

The oxygenator 1 shown in FIG. 1 has a blood inlet 2 and a blood outlet 3. A gas supply is provided by a gas inlet 4 and a gas outlet 5. In the heat exchanger, hollow fibers are provided, through which water flows in the radially inner region, as are semi-permeable hollow fibers, through which gas flows in the radially outer region. By this means, heating takes place in the radially inner region by means of water entering at water inlet 8, and leaving at water outlet 9, while a gas exchange takes place in the radially outer region 7. For a more detailed explanation of such an oxygenator, reference is made to EP 765 683 B1.

Figure 2:
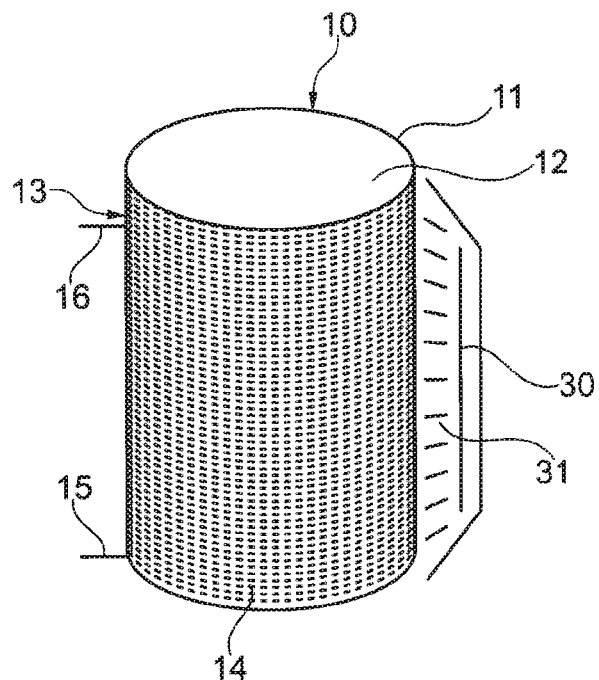
FIG. 2 shows schematically an oxygenator irradiated with infrared light.

In the case of the oxygenator shown schematically in FIG. 2, the basic structure is essentially retained, and the water inlet 8, the water outlet 9 and the hollow fibers through which water flows, are dispensed with. The oxygenator 10 has a housing wall 11 that surrounds a housing space 12. As shown in FIG. 1, this housing space 12 has a blood inlet 2 and a blood outlet 3, and a gas inlet 4 and a gas outlet 5. A semi-permeable matte-black printed surface 14 arranged in the housing wall 11 serves as a receiver 13, which is wound evenly around the housing space 12 in the form of a film. The film 14 forms a receiver, which is heated when a voltage is applied to the electrical terminal connections 15, 16 such that the radiation source 30 emits infrared light 31.

Figure 3:
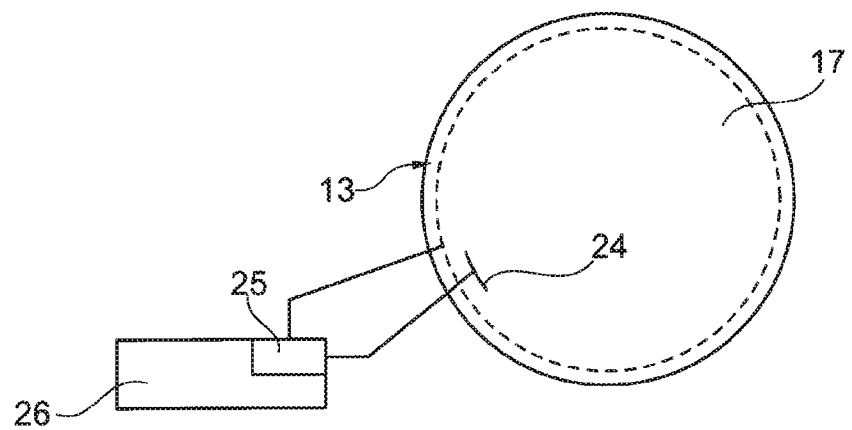
FIG. 3 shows a plan view of the oxygenator shown in FIG. 2.
Figure 4:
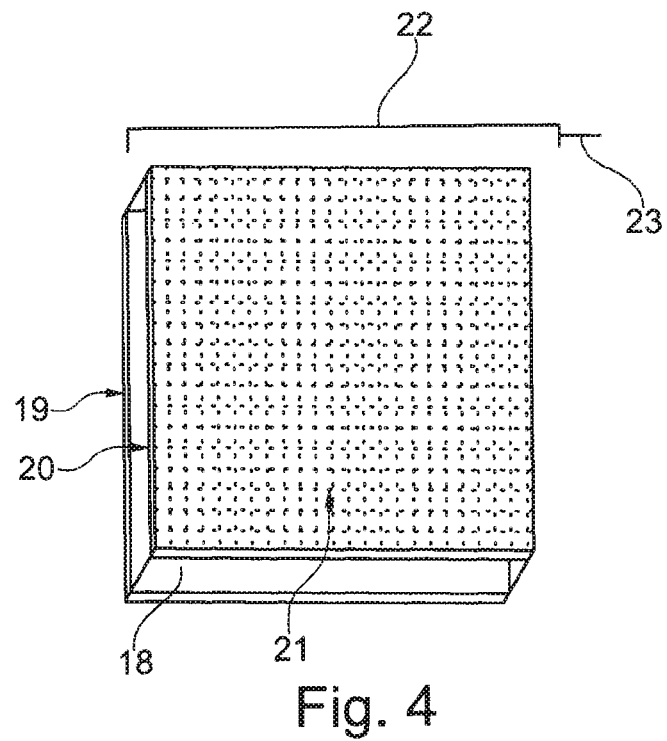
FIG. 4 shows schematically an oxygenator with layered membrane fibro fiber mats and a semi-permeable printed receiver surface.
Figure 5:
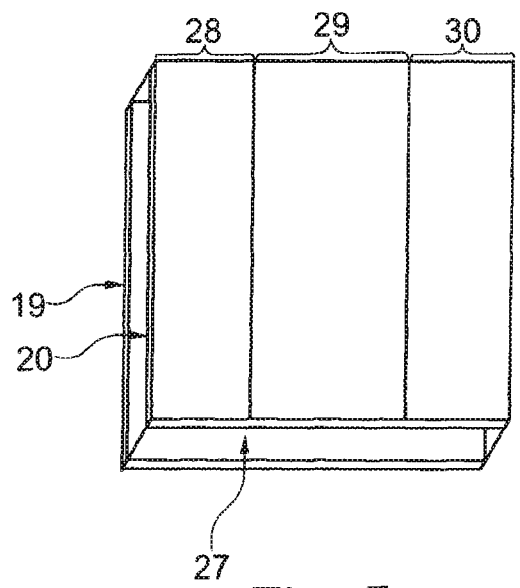
FIG. 5 shows schematically an oxygenator with layered mats and receiver components that can be separately controlled.

The oxygenator can have, as in the examples of embodiment in FIGS. 1 to 3, wound hollow fiber mats 17 arranged in the housing space 12, or, as shown in FIGS. 4 and 5, stacked mats 18 of hollow fiber membranes arranged between two plates 19 and 20. In the example of embodiment shown in FIG. 4, a semi-permeable matte-black printed surface 21 is provided on the upper plate 20. A radiation source 22 is connected to an electrical terminal connection in order to direct infrared radiation onto the printed surface 21.

FIG. 5 shows hollow fiber mats 27 between two plates 19 and 20, of which the upper plate 20 has a semi-permeable matte-black printed surface 21. Schematically three receiver components 28, 29, 30 are indicated, which can have different radiation-absorption capacities, or can be irradiated in different manners, so to produce different amounts of heat at various locations on the oxygenator. In particular, the receiver components 28, 29 and 30 can be controlled such that a certain temperature difference between the receiver component and the blood temperature on the receiver component is not exceeded.

FIG. 3 shows schematically a temperature sensor 24 connected to a temperature regulation device 25 mounted in a control console 26.

In FIGS. 6 to 9 the algorithmic control by time intervals is shown in an optimized form. A model is determined from a real gas exchanger. In this gas exchanger model, which is drawn in FIG. 6 as an oxygenator model 114 for purposes of measurement point location, measurement points are defined and the material properties, required as parameters for the calculations, are determined. The temperature can be measured at all measurement points.

The sensors, blood and gas parameters already present in an ECMO system are fed into the control console. A desired temperature is then compared with a measured temperature, taking into account control console values. This is undertaken individually for each measurement point and each heating element. As a result various tolerances ensue between the measured values and the desired temperatures. The appropriate heating frequency, with frequency of heating occurrence and heating intensity, is then selected from all parameters for each heating element, in order to achieve and subsequently maintain the desired temperature with as little trauma to the blood as possible. These frequencies can be stored in a table to facilitate the control of the oxygenator subsequently.

Figure 6:
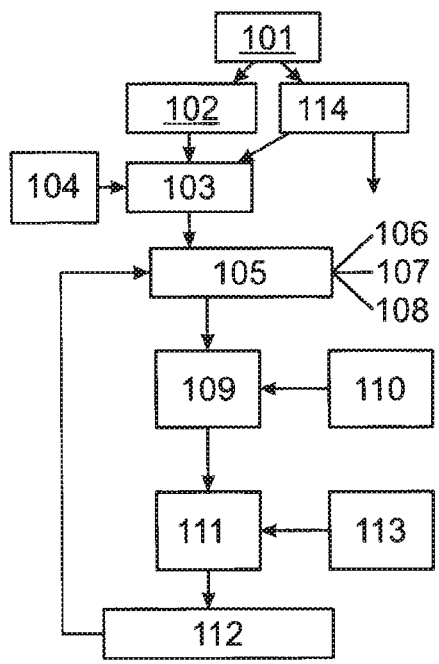
FIG. 6 shows schematically the interaction of components of an algorithm.

In the algorithm shown in FIG. 6, the user 101 sets the desired temperature 102, which is entered into the control console 103. The blood flow, gas flow and pressure parameters 104 are also entered into the control console. The control console initiates a temperature measurement 105 so as to determine average temperatures 106, 107 and 108 at different measurement points of the oxygenator. The comparison 109 between the desired temperature and the average measured temperature at the various locations leads to the difference value. This value is set off against the temperature deviations 110 determined at the various locations, and the control console data such as blood flow. This provides the fundamentals for an individual regulation 111 of the heating elements on the basis of the comparison between the temperature deviations and the control console data. The heating elements 112 can be controlled with these values. In addition, the individual regulation can also be governed by the heating algorithm 113, which is selected from a table and ensues from the measured parameters. In addition, any alteration in the receiver (color, position, switching, etc.) can be used in addition to the heating algorithm, or instead of the heating algorithm, to govern the control process.

The heat output of the heating elements 112 acts on the temperatures 105 measured with the temperature measurement process, resulting in a feedback onto the measured temperatures.

Figure 7:
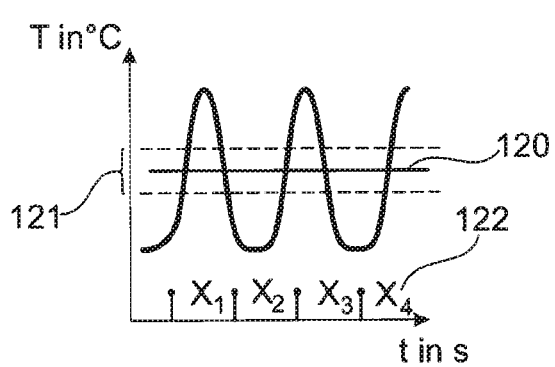
FIG. 7 shows schematically the average temperatures plotted against time.

FIG. 7 shows the desired temperature 120 in a coordinate system with the temperature in ° C. plotted against time in seconds. The lambda value indicates the thermal conductivity, which is influenced by the material constants, and which leads to temperature peaks being absorbed. $X_1$, $X_2$, $X_3$ and $X_4$ are examples of temperature measurement points 122.

Figure 8:
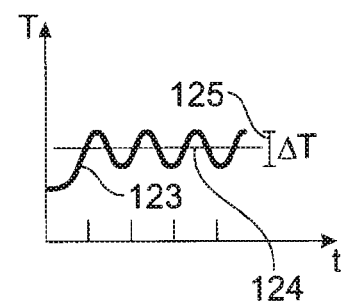
FIG. 8 shows schematically the temperature plotted against time at a first location.
Figure 9:
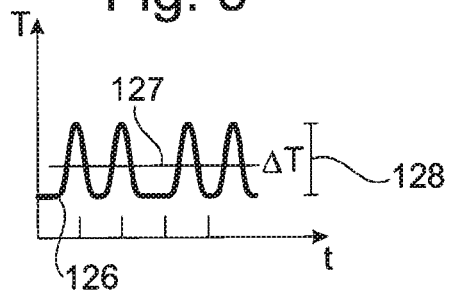
FIG. 9 shows schematically the temperature plotted against time at a second location.

FIGS. 8 and 9 show the temperature profile plotted against time for two measurement points. In FIG. 8 the temperature profile 123 at a first measurement point is plotted against time as a wavy line, which fluctuates about a temperature 124 and defines a delta T ($\Delta T$) 125. Similarly, in FIG. 9, the current temperature 126 at a second location is recorded against an average temperature 127, resulting in a temperature deviation delta T ($\Delta T$) 128.

The invention claimed is:

1. An oxygenator system comprising:
an oxygenator with a housing wall, which delimits a housing space, with a blood inlet, a blood outlet, a gas inlet and a gas outlet, and a heating element to control the temperature of the blood flowing through the housing space,
wherein the heating element has a radiation source and a receiver, which converts the radiation from the radiation source into heat,
wherein the receiver comprises a plurality of receiver elements positioned at different receiver locations of the oxygenator and delivers a different heating power at different housing locations in the housing space, and
wherein the oxygenator further comprises temperature sensors at different sensor locations in the oxygenator; and
a control console connected to the oxygenator, the control console comprising control electronics controlling the oxygenator,
wherein the control console is adapted to receive a desired temperature, to initiate a temperature measurement at different measurement locations of the oxygenator, and to compare the desired temperature to a measured temperature at the different measurement locations of the oxygenator; and
wherein the control console is further adapted to control the radiation source or the receiver or the radiation source and the receiver as a function of the measured temperature.

2. The oxygenator system in accordance with claim 1, wherein the radiation source emits infrared light, and the receiver has a matte-black surface.

3. The oxygenator system in accordance with claim 2, wherein the wavelength of the radiation source is adjustable.

4. The oxygenator system in accordance with claim 1, wherein the radiation source has an induction coil, and the receiver has a material capable of induction.

5. The oxygenator system in accordance with claim 1, wherein the radiation source has a fan.

6. The oxygenator system in accordance with claim 1, wherein the radiation source is a device that can be set apart from the housing space.

7. The oxygenator system in accordance with claim 1, wherein the radiation source is arranged on a housing holder.

8. The oxygenator system in accordance with claim 1, wherein the radiation source is arranged concentrically with the housing space.

9. The oxygenator system in accordance with claim 1, wherein the receiver is arranged in the housing wall.

10. The oxygenator system in accordance with claim 1, wherein the receiver is arranged in the housing space.

11. The oxygenator system in accordance with claim 1, wherein the oxygenator has membranes.

12. The oxygenator system in accordance with claim 1, wherein the receiver is arranged in the oxygenator between the gas inlet and the gas outlet, so as to control also the temperature of gas flowing through the housing space.

13. The oxygenator system in accordance with claim 1, wherein the housing wall has only four fluid passages leading to the external environment.

14. The oxygenator system in accordance with claim 1, further comprising at least one connector, wherein a part of the receiver is arranged in the at least one connector.

15. The oxygenator system in accordance with claim 1, wherein the receiver has a heat conduction device for the distribution of heat from the receiver in the housing space.

16. The oxygenator system in accordance with claim 1, further comprising an insulating layer to insulate the blood flowing in the housing space.

17. The oxygenator system in accordance with claim 16, wherein the layer is transparent.

18. The oxygenator system in accordance with claim 1, further comprising a reflective layer so as to reflect heat radiation from the blood flowing in the housing space.

* * * * *